United States Patent [19]
Ferro

[11] 3,994,293
[45] Nov. 30, 1976

[54] INJECTOR ASSEMBLY FOR USE IN TRANSFUSIONS AND PERFUSIONS

[75] Inventor: Antonio Ferro, Milan, Italy

[73] Assignee: Crinospital S.p.A., Palazzo Pignano, Italy

[22] Filed: Apr. 29, 1975

[21] Appl. No.: 572,644

[30] Foreign Application Priority Data
May 7, 1974 Italy .................................. 22356/74

[52] U.S. Cl. ............................................. 128/214 R
[51] Int. Cl.² .......................................... A61M 5/00
[58] Field of Search ................. 128/214 R, 210, 349, 128/350, 247; 137/513.3, 525.3, 604, 218

[56] References Cited
UNITED STATES PATENTS

| | | |
|---|---|---|
| 3,416,567 | 12/1968 | Von Dardel et al. ................ 137/604 |
| 3,478,743 | 11/1969 | Ericson .......................... 128/349 BV |
| 3,833,154 | 9/1974 | Markowitz ....................... 137/525.3 |
| 3,834,124 | 9/1974 | Ichikawa .............................. 128/214 |
| 3,883,030 | 5/1975 | Mathews .......................... 137/525.3 |
| 3,908,653 | 9/1975 | Kettering ........................ 128/214 R |

Primary Examiner—G.E. McNeill
Attorney, Agent, or Firm—Finnegan, Henderson, Farabow & Garrett

[57] ABSTRACT

An extemporaneous injector assembly for use in transfusions and perfusions comprises a tubular conduit for passage therethrough of a transfusional or perfusional liquid, which is provided with a tubular branch communicating with the conduit for feeding a nourishing solution, a medicinal solution or a like solution into the transfusional or perfusional liquid. A pre-perforated normally impervious diaphragm, which becomes, however, pervious under the action of a prefixed minimum pressure, is positioned in the tubular branch.

5 Claims, 2 Drawing Figures

INJECTOR ASSEMBLY FOR USE IN TRANSFUSIONS AND PERFUSIONS

BACKGROUND OF THE INVENTION

1. Field of the Invention

This invention relates to an extemporaneous injector assembly for use in transfusions and perfusions. More particularly, this invention relates to an injector which can be used in combination with a feeding means (e.g. a syringe) for feeding, into a transfusional or perfusional liquid, a nourishing solution, a vitamin solution, a medicinal solution, an anticoagulant solution or a like solution, wherein penetration of a hollow piercing member (e.g. a syringe needle) into the injector body is not necessary.

2. Description of the Prior Art

It is well known that during transfusions and perfusions, the periodic addition of various substances to the transfusional or perfusional liquid may be desirable or necessary. For instance, in blood transfusions, the addition of an anticoagulant such as heparin is the customary practice. When transfusional reactions occur, the addition of antipyretic agents may be necessary. The commonest of such transfusional reactions is the reaction induced by pyrogens contained in the transfusion liquid or in the devices used for transfusional purposes. The pyrogens are fever-producing substances, i.e. substances capable of inducing in a patient a marked temperature rise accompanied by shivering. As a further instance, there can be mentioned the periodic addition of nourishing solutions containing vitamins to the transfusional liquid fed through the epicranial vein to prematurely born babies.

To carry out such periodic or intermittent additions, devices known as "extemporary (or intermittent) injectors" have heretofore been in general use. These known injectors essentially comprise a tubular portion which is fitted in series in the tubular conduit conveying the perfusional or transfusional liquid to the patient.

The injectors at present in general use are made from elastomeric materials because the connection between the injector and the source of the solution which is intermittently or occasionally to be injected into the perfusional or transfusional liquid is achieved by forced penetration of a hollow piercing member through the injector wall. Usually, a syringe containing the solution to be injected is employed. The needle of the syringe is used to puncture the injector wall and thus to penetrate into the injector body. When the needle is withdrawn upon termination of the addition, the hole formed by the needle closes in view of the elastic nature of the wall, thus ensuring that the injector is sealed. This sealing is possible since the pressure exerted by the circulating liquid on the wall of the tubular conduit is relatively low.

However, the simplicity of the extemporary injectors in use at present results in disadvantages which are attributable to the extremely unsophisticated structure of the injectors.

These disadvantages are essentially due to the fact that every addition of solution, even during the same use of a single injector, requires a new hole to be made in the injector wall. Since, for the sake of economy, the same injector should be used for several perfusions or transfusions, it is apparent that in the long run the injector structure weakens, and that, after many punctures, the injector wall is no longer adequately sealed. It can in fact easily experienced that it is not necessary to repeatedly puncture always the same point of the injector wall to compromise the sealing of a certain zone of the injector. This disadvantage is particularly serious because a lack of sealing might occur suddenly in the course of use when withdrawing the needle after many punctures. In such a case, should the lack of sealing be extensive, the transfusion ought to be discontinued at once.

A further disadvantage of the extemporaneous injectors at present in use is the necessity to use a needle for hypodermic or intravenous injections. The cost of the needles weighs heavily on the general costs of the transfusion unit, particularly in view of the ever increasing frequency of the injections into the perfusional or transfusional liquids.

SUMMARY OF THE INVENTION

According to the present invention, there is provided an extemporaneous injector for use in transfusions and perfusions, comprising a tubular conduit for passage therethrough of a transfusional or perfusional liquid, provided with a tubular branch in communication with the conduit for feedng a nourishing solution, a vitamin solution, a medicinal solution, an anticoagulant solution or a like solution into the transfusional or perfusional liquid; and a pre-perforated elastomeric diaphragm positioned in the tubular branch, the diaphragm being normally impervious to prevent passage of solution and liquid between the branch and the conduit, whilst becoming pervious under the action of a pressure at least equal to a prefixed minimum pressure corresponding to the perviousness threshold of the diaphragm, thus allowing passage of the solution from the branch to the conduit.

It is apparent that in order to feed any solution into an injector having the foregoing structural features, it is not necessary to puncture the injector wall for each addition. It will be sufficient to place close to the pre-perforated diaphragm, by fitting it into the tubular branch, any means suitable for delivering to the diaphragm the solution to be introduced into the perfusional or transfusional liquid which is conveyed along the tubular conduit, under a pressure sufficient to cause temporary perviousness of the pre-perforated diaphragm, thus establishing a temporary passage between the branch and the tubular conduit. Upon termination of the feeding of the solution, or upon decreasing the pressure exerted by the solution upon the diaphragm to a pressure below the perviousness threshold of the diaphragm, the passage between the branch and the tubular conduit is closed, i.e. the sealing by the diaphragm is restored.

As used herein, the term "perviousness threshold" means the minimum pressure which must be exerted on the diaphragm in order to cause it to become pervious.

It is apparent that the perviousness threshold depends on several factors which are, however, easily ascertainable by those skilled in this art. These factors are, for example, the specific nature of the elastomeric material constituting the diaphragm, the diaphragm thickness, and the nature of the pre-perforation in the diaphragm.

Regarding the material constituting the diaphragm, there can be used any elastomer which in use is compatible with and chemically inert to both the transfusional liquid and the nourishing solution, the vitamin solution, the medicinal solution, the anticoagulant solution or the like solution to be introduced in the liquid. Examples of suitable elastomers are natural rubber, polybutadiene; butadiene-styrene copolymers; butadiene-acrylonitrile copolymers; and ethylene-alphaolefin copolymers, particularly elastomeric ethylene-propylene copolymers.

The thickness of the diaphragm can vary within a wide range. Usually, diaphragms having thickness between about 0.5 and about 3 millimeters, preferably between 1 and 2 millimeters, are used.

Pre-perforation of the diaphragm is preferably carried out by puncturing the diaphragm by means of a piercing element, typically the needle of a syringe for hypodermic or intravenous injections. Usually, the needle diameter will be between about 1 and 1.5 millimeters. It is apparent that the pre-perforated diaphragm can have one or more perforations. Also, the shape of the perforation or perforations is irrelevant, provided that the diaphragm becomes pervious under a pressure at least equal to the perviousness threshold of the diaphragm.

It is also apparent that the perviousness threshold of the pre-perforated diaphragm may be such that the means for feeding the nourishing solution, the vitamin solution, the anticoagulant solution or the like solution to the diaphragm is able to exert a pressure at least equal to the perviousness threshold. Because such feeding means typically consists of the barrel and plunger (but not the needle) of a conventional syringe for hypodermic or intravenous injections, it will be obviously necessary to ensure that the perviousness of the pre-perforated diaphragm is such that the diaphragm becomes pervious under the pressure which is normally exerted when operating the syringe plunger by hand.

Moreover, it might be advantageous to equip the pre-perforated diaphragm with a suitable unidirectional valve means which permits passage of the solution from the tubular branch into the tubular conduit conveying the transfusional or perfusional liquid, but not vice versa.

DESCRIPTION OF THE PREFERRED EMBODIMENT

Figure 1:
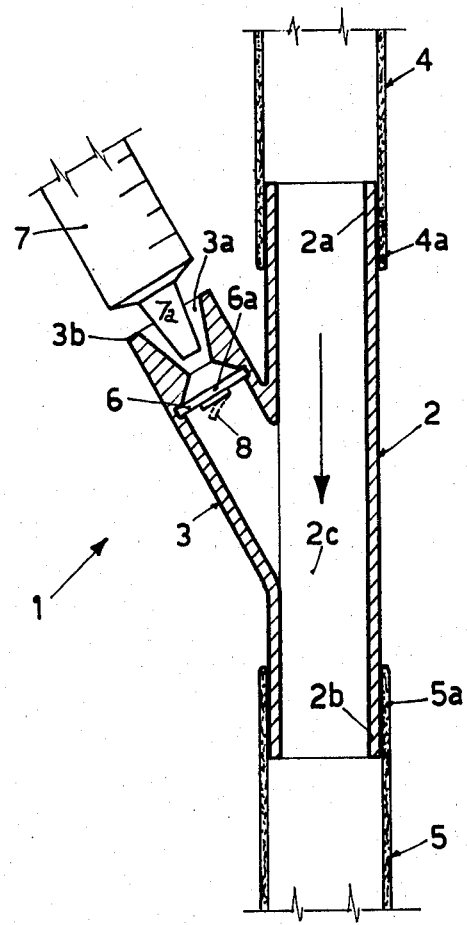
FIG. 1 is a longitudinal sectional view of an extemporaneous injector according to the invention.

Referring to FIG. 1, an extemporaneous injector according to the invention, generally designated by the reference numeral 1, is shown. Injector 1 comprises a tubular conduit 2 provided with a tubular branch 3 in communication with the conduit for feeding a solution containing the desired nourishing agent, vitamin, medicinal agent, anticoagulant or the like agent into the perfusional or transfusional liquid conveyed through tubular conduit 2 in the direction shown by the arrow. Tubular conduit 2 is inserted in series in a conduit for transferring the perfusional or transfusional liquid from a source thereof (not shown) to a patient (not shown). Thus, end 2a of the tubular conduit fits into the end 4a of a tubing 4 connected at its opposite end to a reservoir of perfusional or transfusional liquid, whilst end 2b fits into the end 5a of a tubing 5 connected at its opposite end to a patient. Tubular conduit 2 and tubular branch 3 can be manufactured by moulding, in a single piece, a suitable plastics material which is chemically inert to both the transfusional or perfusional liquid and to the nourishing solution, the vitamin solution, the medicinal solution, the anticoagulant solution or the like solution. For instance, in order to manufacture the tubular conduit and its tubular branch integral therewith, reinforced polyvinylchloride could be used. Other suitable materials will be apparent to those skilled in this art.

A pre-perforated diaphragm 6 made of an elastomeric material closes the passage between the inner zone 3a of branch 3 and the inner zone 2c of tubular conduit 2 under normal conditions, i.e. when the pressure urging on the diaphragm is lower than its perviousness threshold. Diaphragm 6, which has been previously perforated at 6a, e.g. by means of a 1.4 mm needle, becomes pervious under the pressure exerted by a solution, e.g. a heparin-containing solution, which is injected by syringe 7 in the inner zone 3a of tubular branch 3. In order to provide a seal between the barrel point 7a of syringe 7 and the end portion 3b of tubular branch 3, the inner wall of end portion 3b is shaped so as to receive snugly the substantially frust-conical outer wall of barrel point 7a. Pre-perforated diaphragm 6 can be provided with valve means permitting unidirectional flow from 3a to 2c, but not vice versa. Thus, as shown in FIG. 1, diaphragm 6 is provided on its face contacting the transfusional liquid with a layer 8 made of elastomeric material and fixed to the diaphragm only at one of its edges in such a way that the free portion of layer 8 covers the pre-perforated zone of diaphragm 6. When the pressure inside tubular conduit 2 is higher than the outer pressure, the whole of layer 8 adheres to diaphragm 6, thus enhancing its sealing action. On the other hand, when a solution is injected by means of syringe 7, the pressure at 3a is higher than the pressure exerted by the perfusional or transfusional liquid at 2c and, in particular, exceeds the perviousness threshold of the pre-perforated diaphragm 6, whereby layer 8 moves to the position shown by the dotted line in FIG. 1, thus permitting passage of the solution into injector 1.

Figure 2:
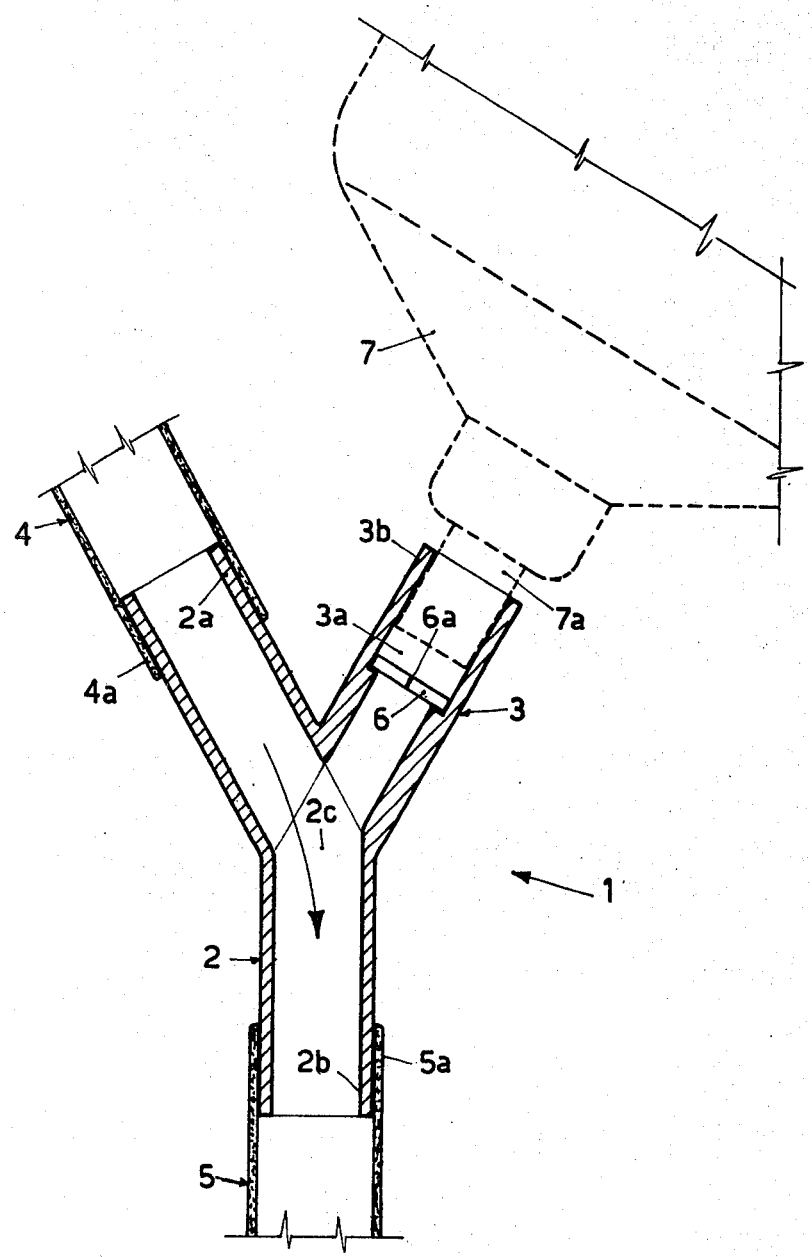
FIG. 2 is a longitudinal sectional view of another extemporaneous injector according to this invention.

In FIG. 2, wherein like elements are designated by the same reference numerals as in FIG. 1, a second extemporaneous injector according to this invention is shown, wherein the portion of the tubular conduit forms with tubular branch 3 a Y-shaped structure.

The extemporaneous injector shown in the drawings are simple and inexpensive, and do not need to be repeatedly punctured in order to feed into the injector any solution to be added to a transfusional or perfusional liquid, whereby destruction of the diaphragm is avoided. The injectors shown in the drawings also enable the user to feed the desired solution into a transfusional or perfusional liquid using a simple syringe barrel and plunger according to conventional procedures, without the need to use hypodermic needles.

What I claim is:

1. An extemporaneous disposable fluid injector for use in transfusions and perfusions comprising:
   a. a one-piece Y-shaped tubular member for mixing two liquids together and transmitting the mixture of the two liquids, said member having
      i. a tubular conduit portion for feeding and transmitting therethrough a transfusional or perfusional liquid; and
      ii. a tubular branch portion connected with said tubular conduit for feeding a nourishing, vitamin, medicinal, anticoagulant, or like liquid solution into the transfusional or perfusional liquid in said tubular conduit; and b. a liquid pressure-actuated elastomeric diaphragm positioned in said tubular branch portion, said diaphragm including a pre-perforated portion formed having a pressure threshold corresponding to a predetermined pressure of the solution upstream of said diaphragm wherein said pre-perforated portion is normally impervious to prevent passage of the solution through said tubular branch portion to said tubular conduit portion when the pressure of the solution upstream of said diaphragm is less than said pressure threshold and wherein said pre-perforated portion becomes pervious to allow passage of the solution through said tubular branch portion to said tubular conduit portion when the pressure of the solution upstream of said diphragm is at least equal to or greater than said pressure threshold.

2. The injector of claim 1 further including valve means cooperating with said pre-perforated portion of said diaphragm for permitting only unidirectional feeding of the solution in said tubular branch portion through said pre-perforated portion to said tubular conduit portion.

3. The injector of claim 1, in combination with means for exerting on the pre-perforated portion of said diaphragm a pressure at least equal to the pressure threshold of the diaphragm; and in combination with means for feeding the nourishing solution, the vitamin solutions, the medicinal solution, the anticoagulant solution or like solution to the diaphragm.

4. The injector of claim 3, wherein the pressure means and the feeding means comprise a syringe barrel.

5. The injector of claim 4, wherein the inner wall of the end portion of the tubular branch portion is shaped to snugly receive the barrel point of the syringe barrel.

* * * * *